United States Patent
McLoskey et al.

(10) Patent No.: US 7,582,882 B2
(45) Date of Patent: **\*Sep. 1, 2009**

(54) SOLID STATE MULTI FREQUENCY FLUOROMETRIC MEASUREMENTS SYSTEM AND METHOD

(75) Inventors: David McLoskey, Edison, NJ (US); Glenn Baker, Edison, NJ (US); Jim Mattheis, Edison, NJ (US); Sal Atzeni, Edison, NJ (US)

(73) Assignee: Horiba Jobin Yvon, Inc., Edison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/184,407

(22) Filed: Jul. 19, 2005

(65) Prior Publication Data

US 2006/0022145 A1 Feb. 2, 2006

Related U.S. Application Data

(63) Continuation-in-part of application No. 10/763,681, filed on Jan. 23, 2004, now Pat. No. 7,317,194.

(60) Provisional application No. 60/442,036, filed on Jan. 23, 2003.

(51) Int. Cl.
G01N 21/62 (2006.01)
G01N 21/64 (2006.01)

(52) U.S. Cl. .................. 250/458.1; 250/459.1; 356/317; 356/318

(58) Field of Classification Search ............. 250/201.3, 250/458.1, 459.1; 356/317, 318, 417, 484; 600/473, 476, 407
See application file for complete search history.

(56) References Cited

U.S. PATENT DOCUMENTS

| | | | | |
|---|---|---|---|---|
| 5,257,202 A | * | 10/1993 | Feddersen et al. | 702/32 |
| 5,865,754 A | | 2/1999 | Sevick-Muraca et al. | 600/476 |
| 5,981,957 A | * | 11/1999 | Cruce et al. | 250/458.1 |
| 6,496,267 B1 | | 12/2002 | Takaoka | 356/497 |
| 6,741,346 B1 | * | 5/2004 | Gerstner et al. | 356/318 |
| 2002/0072677 A1 | * | 6/2002 | Sevick-Muraca et al. | 600/473 |
| 2004/0156053 A1 | * | 8/2004 | Wolleschensky et al. | 356/485 |

* cited by examiner

*Primary Examiner*—Georgia Epps
*Assistant Examiner*—Pascal M Bui-Pho
(74) *Attorney, Agent, or Firm*—Thompson Hine LLP

(57) ABSTRACT

A method of spectrographic measurement is disclosed. The method generates light energy using a solid state low capacitance excitation source, the light energy being caused to fall on a sample to be assayed, causing the sample to output an output optical signal. The method generates a plurality of modulation frequencies, and a plurality of heterodyne frequencies to form a set of heterodyne signals at the heterodyne frequencies. Each of the heterodyne frequencies is associated with one of the modulation frequencies. Coupling the modulation frequencies to the excitation source, causes the excitation source to generate excitation energy modulated in intensity in proportion to the modulation frequencies. A sampling a portion of the substantially incoherent excitation energy forms a reference substantially incoherent excitation signal.

Focusing the output optical signal as an image modulated with the plurality of modulation frequencies on an image intensifier enables the formation of an intensified image modulated with the plurality of modulation frequencies, receiving the intensified image modulated with the plurality of modulation frequencies on a multielement optical detector.

22 Claims, 3 Drawing Sheets

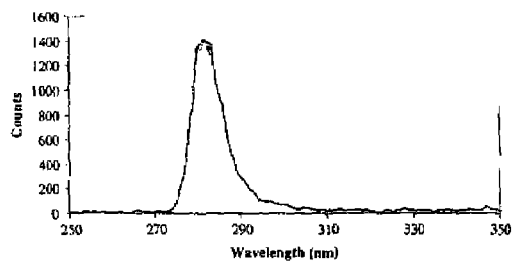
Figure 1.
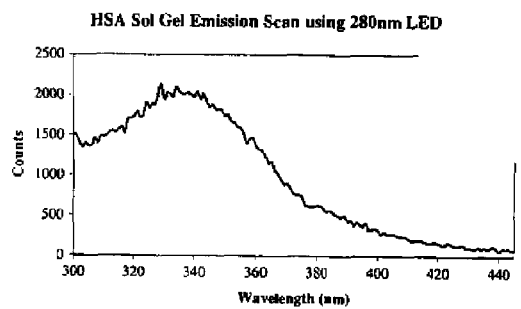
Figure 4.
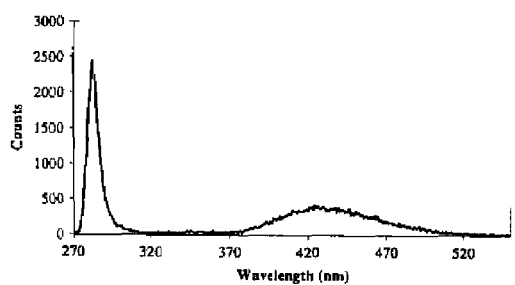
Figure 2.
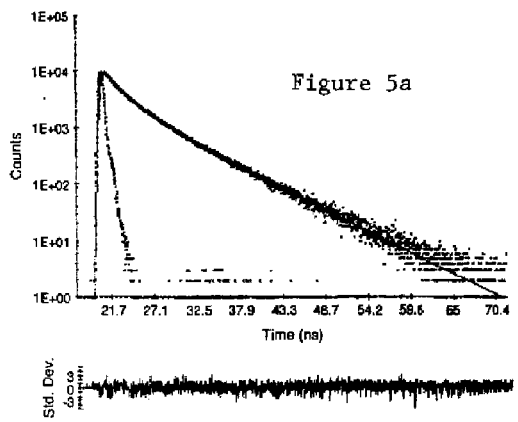
Figure 5a
Figure 5b
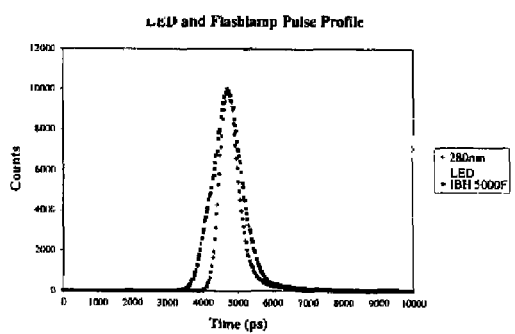
Figure 3

SOLID STATE MULTI FREQUENCY FLUOROMETRIC MEASUREMENTS SYSTEM AND METHOD

CROSS REFERENCE TO RELATED APPLICATIONS

This application is a continuation in part of U.S. patent application Ser. No. 10/763,681, filed: Jan. 23, 2004 now U.S. Pat. No. 7,317,194, which claims benefit of U.S. Provision patent application No. 60/442,036, filed: Jan. 23, 2003.

TECHNICAL FIELD

The present invention relates to frequency domain measurements employing using a low cost, low complexity 295 nm light modulated in intensity with a plurality of frequencies, employing a solid-state light emitting source, and is particularly suited for the investigation of certain biological entities.

BACKGROUND

The characteristics of light emanating from an object or a material may be advantageously detected and analyzed in order to determine characteristics of the object or material under examination. For many years, spectrographic techniques have been used to perform analysis of materials ranging from human blood and other biological materials to slag from a crucible. For example, it has been known that wavelengths of light absorbed by a material, as well as the wavelengths of light emitted by a material during an excited state, such as combustion, both indicate the composition of the material. Today, analytic instruments in industrial, scientific and medical applications make widespread use of such emission spectra and absorption spectra. Another such technique is Raman spectroscopy, where, for example, the output of a mercury vapor arc lamp may be filtered and used to excite a transparent material. As the light transmits through the material, it is scattered and undergoes a change in wavelength and a random alteration in phase due to changes in the rotational or vibrational energy of the sample. Raman scattering is a principal analytic tool in industry and science today.

A specific class of analytic instruments uses fluorescence (or phosphorescence) to identify materials. In such systems, an excitation source, such as a laser, is used to excite atoms or molecules, raising electrons into higher energy states. When the electrons revert back to the unexcited state, they fluoresce or emit photons of light characteristic of the excited atom or molecule. In addition, the time delay between the exciting light and the emitted light, as well as the amplitude of the emitted light, provide information about the material's composition, lifetimes, and concentration of various components. Instruments that provide this function are known as frequency domain fluorometers or time correlated single photon counting instruments (TCSPC).

Frequency domain fluorometers rely on phase delay and amplitude measurements. The exaltation source is modulation which causes the re-emission of a fluorescent signal and it is the relationship between the re-emission (phase delay) and reduction in modulation which is used to calculate the lifetime. In one class of instruments such measurements may be achieved by frequency modulating a light source. For example, one may employ for this purpose a pulsed dye laser, or a continuous wave laser whose output is externally modulated by a Pockels cell or an LED which is intrinsically modulated.

By "phase" is meant the re-emission delay in degrees or time, of the modulated fluorescence emission of an unknown sample as compared to a modulated reference, which may be either the excitation source or a known sample. By "modulation", sometimes also referred to as the modulation ratio, is meant the ratio of the amplitude of a fixed reference, either a known sample or the excitation source, to the fluorescence amplitude of the unknown sample. A further refinement of the measurement technique is to perform the measurement of modulation and phase on a sample many times using different modulation frequencies each time. Generally, this results in the generation of a first characteristic for phase as a function of modulation frequency and a second characteristic of modulation as a function of modulation frequency. Generally, phase angle will increase with increasing modulation frequency. Moreover, for samples exhibiting longer lifetimes, phase will be larger at a given modulation. Similarly, modulation tends to decrease for samples exhibiting longer lifetimes, at a given modulation frequency.

If curve fitting techniques are used to match the plot of frequency versus phase and the plot of frequency versus modulation, to a pair of equations, analysis of the equations can be used to discern multiple individual fluorescing components, for example organic molecules, fluorescing semiconductor depositions or dopants or the like, in a sample. Curve fitting techniques are known in the field today and generally involve the use of a digital computer to perform the desired curve fitting and the comparison of various physical models that represent the molecular system and its environment.

Frequency domain cross-correlation techniques are well developed in the prior art (e.g. U.S. Pat. Nos. 4,840,485, 5,151,869 and 5,196,709 etc.) and commercial instruments are available for sale. The downside of these techniques are that each frequency is individually scanned, and this is a slow process. Additionally only one detector at a time is used, and one loses any spatial relationships within the samples.

To maintain the spatial relationships with the sample another technique has been developed called fluorescence lifetime imaging microscope (FLIM), using a single frequency domain instrument coupled to a camera using homodyne and sometimes heterodyne detection.

A further improvement on these technique was disclosed by Mitchell in U.S. Pat. No. 4,937,457. Mitchell disclosed a technique of producing multiple coherent harmonics to speed up the process of data collection. In these instruments, fluorescence measurement is obtained by deriving phase and modulation information in the steady state from a fluorescence or phosphorescence emission driven by a light source modulated with multiple modulation frequencies.

In another class of instruments, which rely on time-domain lifetime measurement, a time correlated single photon counting (TCSPC) method is employed. In this type of instrument, a measurement is made of the probability of a fluorescent photon emission after the fluorophore receives an excitation pulse. The measurement is made by counting the arrival time of individual photons within certain time periods after emission.

The light sources for both of these instruments suffer from similar drawbacks; are expensive and their light sources can be large and require special facilities and operator training and so forth.

In accordance with the invention a method of spectrographic measurement comprises generating light energy using a solid state low capacitance excitation source. The light energy is caused to fall on a sample to be assayed, causing the sample to output an output optical signal. A plurality of modulation frequencies are generated. In addition, a plurality of heterodyne frequencies are generated to form a set of heterodyne signals at heterodyne frequencies. Each of the heterodyne frequencies is associated with one of the modulation frequencies. The modulation frequencies are coupled to the excitation source, causing the excitation source to generate excitation energy modulated in intensity in proportion to the modulation frequencies. A portion of the substantially incoherent excitation energy is sampled to form a substantially incoherent reference excitation signal. The output optical signal is focused as an image modulated with the plurality of modulation frequencies on an image intensifier. The image is intensified to form an intensified image modulated with the plurality of modulation frequencies. The intensified image modulated with the plurality of modulation frequencies is received on a multi-element optical detector. A plurality of measurement signals are generated using the multi-element optical detector. Each measurement signal is associated with one of the elements. Each measurement signal associated with one of the elements of the multi-element optical detector is mixed with the heterodyne signal to generate a plurality of low-frequency measurement modulation products. A low-frequency measurement modulation product is associated with each of the modulation frequencies and comprises the difference between a single modulation frequency and its associated heterodyne frequency and has a measurement amplitude and phase. The substantially incoherent reference excitation energy is mixed with the heterodyne signal to generate a plurality of reference modulation products, one reference modulation product being associated with each of the modulation frequencies and comprising the difference between a single modulation frequency and its associated heterodyne frequency and having a reference amplitude and phase, each of the low-frequency reference modulation products being associated with one of the measurement modulation products. Each of the plurality of low-frequency measurement modulation products is compared to its associated low-frequency reference modulation product to generate an output signal indicating characteristics of the sample at the region on the sample associated with each of the elements.

BRIEF SUMMARY OF THE INVENTION

It has been observed by others that 295 nanometers is close to the absorption peak of tryptophan, and the present invention contemplates measurements of such proteins using light emitting diodes (LED) operating in this range. Moreover, in accordance with the invention the same is achieved by the measurement of proteins in silica sol-gels, without the expected effects of scattered excitation or scattered fluorescence, notwithstanding the porous nature of the sol gel medium.

While fluorometric frequency domain fluorometricers methods using semiconductor laser diodes in a frequency domain configuration are known, for example from U.S. Pat. No. 5,196,709 of Berndt, the same have not seen substantial application on account of inherent limitations flowing from problems associated with the frequency domain detection and characteristics of the laser sources used therein.

Some work recently has been done using LEDs in the visible, but the same is not a viable solution due to slow response time.

Accordingly, the standard for TCSPC measurements is the use of a flashlamp. In TCSPC measurements, the electrodes of the flashlamp require regular cleaning and the flashlamp requires regular gas replenishment. In addition to these problems, the lower repetition rate of a flashlamp, typically in the range of about 40 kilohertz increases the potential for radio frequency distortion of decays due to higher voltage switching and poorer pulse-to-pulse temporal reproducibility.

In principle, the inventive system provides a method of luminescence time-resolved measurement which, compared to prior art systems, greatly reduces the time required to observe protein interactions, while simultaneously reducing the cost and complexity of the system, while improving both sensitivity and time resolution. In particular, in accordance with the invention, a fluorescence measurement system particularly suited for imaging and making other fluorescence measurements for proteins comprises a 295 nm LED as an excitation source, a frequency domain fluorometer or TCSPC instrument, a sample illuminated by this excitation source, and a detector sensitive to a range of wavelengths of interest, for example those in the range of about 295-450 nm. The informational output which is obtained using such a system contains unique information on protein dynamics. Such protein dynamics include the measurement of energy transfer, lifetimes, folding, and various energy activities.

While, as alluded to above, the use of laser diodes has been considered in the past such diodes are relatively uneconomical and available wavelengths are limited. In addition, while the application of light emitting diodes to frequency-domain fluorescence microscopy has also been considered in the past, generally, such devices have capacitances which are too large to enable them to successfully implement frequency-domain or even time correlated single photon counting measurements.

The inventive use of a laser diode operating at 295 nanometers allows a number of key applications by using 'intrinsic' tryptophan fluorescence lifetimes, be they natural or engineered try mutations, as fluorescence probes for protein investigations. This is because tryptophan fluorescence intensity and the average lifetime is sensitive to the pH of the surrounding environment, making it an excellent pH probe. Moreover, tryptophan fluorescence has two emission spectral components with separate lifetime decays. Previous instruments have found these two components difficult to resolve. The inventive system facilitates resolution of these two components by virtue of its high sensitivity. Moreover, in addition tryptophan fluorescence can be quenched by several chemicals in solution including oxygen and iodide. Hence, in accordance with the invention the location and exposure of the intrinsic tryptophan to its outside environment, in the context of the protein, can be probed with these quenchers. This functionally allows the tryptophan fluorescence lifetime to provide key tertiary and quaternary information concerning the protein folding, structure and aggregation characteristics. In addition to this, tryptophan can accept energy down-hill from tyrosine hence fluorescence resonance energy transfer data can provide important distance information helping to interpret structural information about protein folding and structure. It is further noted that tryptophan fluorescence is sensitive to anisotropic conditions. Accordingly, solvent characteristics and or binding of protein subunits and oligomerization can be studied as changes in the rotation/polarization of the tryptophan fluorescence lifetime.

In addition, the present invention provides measurements which are independent of changes in fluorophore concentration due to the effects of photobleaching. At the same time, the ease of measurement, the availability of time discrimination and kinetic rates together with unambiguous calibration increase the attractiveness of the inventive method.

It is expected that the inventive technique of protein intrinsic fluorescence, decay measurement and its associated observation of fluorescence anisotropy, collisional quenching and resonance energy transfer make it a key tool available to the protein researcher.

BRIEF DESCRIPTION OF THE DRAWINGS

The advantages, and the method for implementing the present invention will be understood from the following description taken together with the drawings, in which:

FIG. 1 illustrates an LED spectral profile with an actual peak at about 282 nanometers in accordance with the method of the present invention;

FIG. 2 illustrates the full LED spectral profile;

FIG. 3 illustrates LED and flash lamp pulse profile;

FIG. 4 illustrates a human serum albumin sol gel emission scan using a 280 nm light emiting diode generated using the inventive method;

FIGS. 5*a*-*b* illustrate the fluorescence decay of human serum albumin in the hydrated sol gel using 280 nanometer light emitting diode excitation;

DETAILED DESCRIPTION OF THE PREFERRED EMBODIMENT

Figure 6:
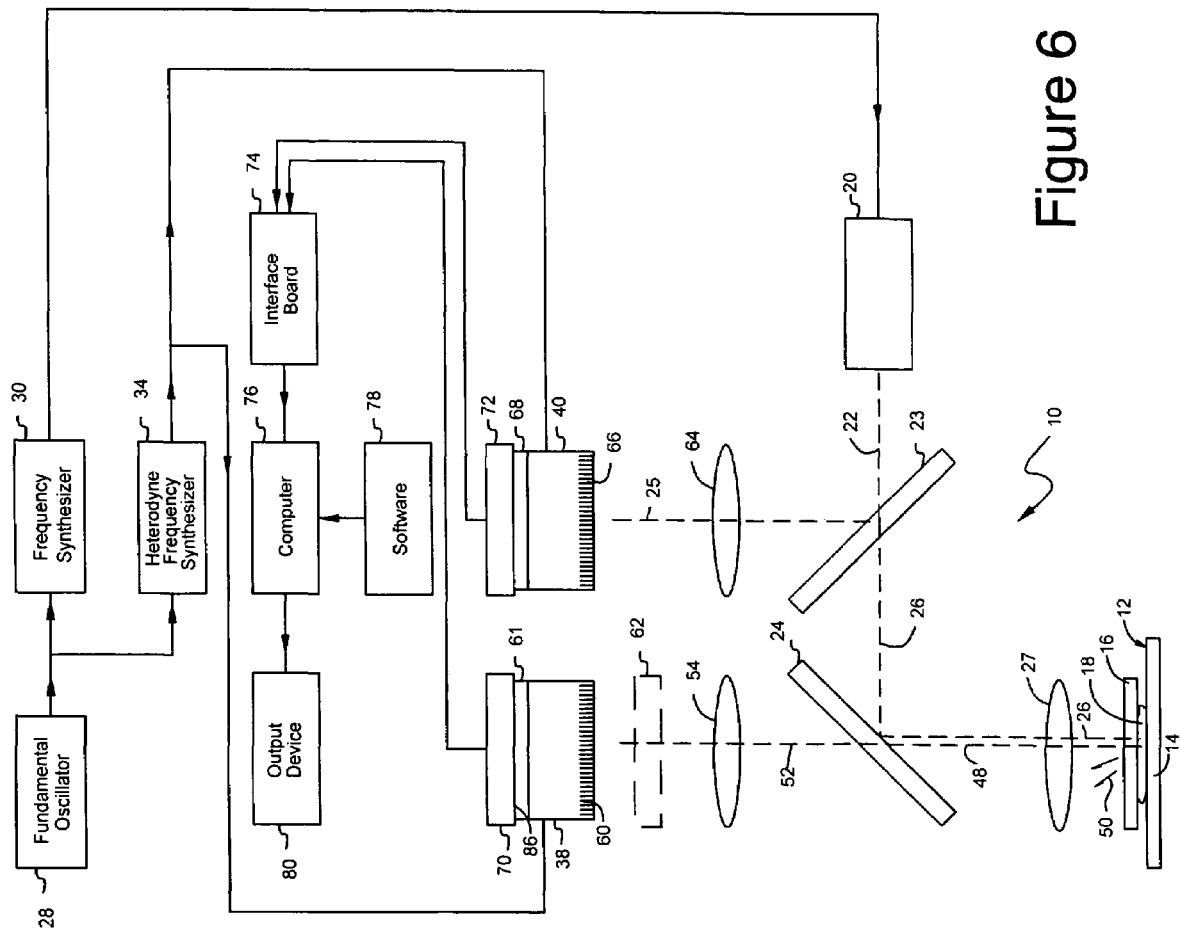
FIG. 6 illustrates a system for implementing the inventive method in the frequency domain.

In accordance with the present invention, fluorescence decay is measured by the observation of the native fluorescence of the proteins, such as the amino acids tyrosine and tryptophan. This represents significant advantages as compared to the use of an extrinsic fluorescent probe which carries with it the possibility of disturbing the local environment. As noted above, the present invention has significant advantages as compared to the prior art techniques for exciting intrinsic protein fluorescence, including synchrotron radiation, mode locked lasers and flashlamps. The present invention allows the accumulation of data at a faster rate as well as simplified, less labor-intensive data generation.

More particularly, in accordance with the present invention, fluorescence measurements of protein intrinsic fluorescence, excited using a light emitting diode operating with an output wavelength below 350 and more particularly below 300 nanometers may be taken on human serum albumin contained within a sol gel sensor matrix.

In accordance with the invention, time correlated single photon timing was used to gather fluorescence data. IBH reconvolution software was used to analyze fluorescence decays. Measurements may be taken in accordance with the present invention using nitride semiconductor light emitting diodes (such as those marketed by Sensor Electronic Technology, Inc. of Columbia, S.C. under its UVTOP trademark) (such as the UVTOP-295). These laser diodes emit at wavelengths spanning the visible-ultraviolet boundary and down to the deep ultraviolet range and have the advantage of low input capacitance and a correspondingly fast response.

Thus, the inventive system has substantial advantages over the prior art. Besides being far less expensive than comparable laser diode devices, the inventive system has emission response times which allow superior performance. In contrast, existing frequency domain fluorometers and TCSPC instruments operate with less optimal excitation sources at this wavelength, such as modulated continuous wave sources and filters with their attendant high cost and low output of photons, pulsed lasers which have a high cost and complexity, pulsed lamps which are expensive, highly complex to operate and have a very low output of photons, and other LEDs with wavelengths or capacitances not suitable for the excitation of proteins or capable of measuring picosecond lifetimes.

The end result of the inventive system is a low-cost system with high energy output at 295 nanometers, which is ideal for the taking of measurements and imaging of proteins. The system is not complex, requiring no special facilities or training to run and maintain. Moreover, the system may be pulsed at one nanosecond or modulated at frequencies greater than 300 megahertz and enables time resolution of approximately 10 picoseconds.

The data accumulation rate in TCSPC is proportional to the source repetition rate, but is limited to approximately two percent of the source repetition rate if pile-up effects are to be avoided. In accordance with the present invention, it has been found that a source repetition rate of approximately one megahertz is sufficient to accumulate the fluorescence decay of most samples in a few minutes. However, in single molecule and imaging applications higher repetition rates are preferred.

In accordance with the inventive method, AlGaN fabrication techniques are used to implement a light emitting diode in the near ultraviolet through deep ultraviolet range. A typical LED spectral profile with an actual peak at 282 nanometers is illustrated in FIG. 1 as recorded with an IBH f/3 monochromator with a two nanometer bandwidth and incorporating a holographic grating in a Seya-Namioka geometry. The full width at half maximum (fwhm) is approximately 10 nanometers.

FIG. 2 shows the full LED spectral profile, including a longer wavelength emission peak at 430 nanometers. The 430 nanometer peak cannot be used for exciting other fluorophores because of a long decay time in the range of 500 microseconds. Accordingly, it is necessary to use a cutoff filter to select the 280 nanometer band in order to avoid interference caused by the 430 nanometer peak together with the Stokes shifted fluorescence.

In accordance with the invention, this may be achieved using a monochromator to pre-filter the LED excitation at 280 nanometers, before allowing the excitation light to illuminate the specimen under study. Additional discrimination against detecting the effects of the 430 nanometer emission peak is provided by an additional monochromator selecting fluorescence stimulated by the 282 nanometer excitation wavelength.

FIG. 3 shows the LED pulse profile at 280 nanometers measured using photomultiplier detection and time-correlated single photon counting for a typical instrumental pulse, and recorded using an IBH TBX-04 detector under TCSPC conditions at a time calibration of 27 picoseconds per channel, as used for all the time-domain measurements herein. Here the fwhm was approximately 600 picoseconds. A typical pulse from a hydrogen flashlamp is shown for comparison purposes.

In accordance with the invention, human serum albumin in a matrix of tetramethylorthosilicate (TMOS) was prepared at pH 7.5 using standard hydrolysis and condensation reactions as reported by Brinkler and Scherer in Sol Gel Science: The Physics and Chemistry of Sol Gel Processing (Academic), 1990. An excitation source comprising a 280 nanometer light emitting diode in an IBH Model 5000U fluorimeter produced a high quality fluorescence emission spectrum for the human serum albumin without artifacts as illustrated in FIG. 4. The excitation wavelength had a spectral bandwidth of six nanometers.

In accordance with the invention, the inventive use of an excitation wavelength below 300 nanometers to excite blood proteins in silica sol gels into fluorescence is of particular value because of the biocompatibility and nanometer pore size of the sol gel, facilitating immunoassay of analytes, such as metal ions, glucose etc. by preventing protein aggregation, transport of analytes of interest and exclusion of high molecular weight interferents, such as extraneous protein.

FIG. 5 illustrates the fluorescence decay of human serum albumin in the hydrated sol gel using 280 nanometer light emitting diode excitation recorded with an IBH Model 5000U fluorometer equipped with excitation and emission monochromators. The emission monochromator was tuned to transmit 335 nanometers in order to select out the protein fluorescence. The log scale shows sharp LED pulses free from afterglow or after pulsing. For this sample, the fluorescence decay could be accumulated in approximately 2.5 minutes to 7.5 minutes depending on the actual light emitting diode used. The triple decay parameters of 0.53+0.05 nanoseconds, 2.43+0.15 nanoseconds, 6.07+0.05 nanoseconds (errors all three standard deviations) and relative intensities 8%, 38%, 54%, respectively, were found to be consistent with work in other laboratories using, for example a mode-locked laser or a hydrogen flashlamp.

The quality of the goodness of fit showed the data to be free from effects of scattered excitation or scattered fluorescence as might be expected for a porous medium. Preliminary measurements of a range of a light emitting diodes at one megahertz suggested that up to 12 times higher protein fluorescence counts can be obtained as compared to a hydrogen flashlamp at 40 kilohertz.

It is noted that as well as direct tryptophan excitation at 280 nanometers, energy transfer from tyrosine to tryptophan also occurs. While 280 nanometer excitation is ideal for tyrosine excitation, fluorescence measurements on tryptophan are preferably carried out in accordance with the invention using a 295 nanometer light emitting diode which is closer to the absorption of peak of tryptophan. A UVTOP295 driven by IBH NanoLED circuitry available on the market in connection with longer wavelength devices was found to work well for the particularly preferred embodiment of the invention. In accordance with the invention, a 280 nanometer excitation wavelength from a light emitting diode may be used to excite other fluorophores, including naphthalene, stilbene and so forth.

Referring to FIG. 6, a frequency domain fluorescence microscope system 10, constructed in accordance with the present invention, is illustrated. It is noted that the inventive system may be applied to fluorescence and phosphorescence systems and measurements. In particular, a slide 12 comprises a glass slide base 14 and a glass cover 16. Sample 18, which may be liquid, or a solid or dry material, is positioned between glass slide base 14 and glass cover 16. Alternatively, a solid gel matrix may also be used in place of a microscope slide.

Sample 18 is illuminated by a source of light such as solid-state diode 20, which outputs a beam 22 of light which illuminates sample 18 as described below and illustrated in FIG. 6. Beam 22 may be prefiltered, using a monochromator in the manner described above. Diode 20 outputs light at 295 nanometers if the prime objective is tryptophan. On the other hand, if one wishes to a examine a protein such as tyrosine, diode 20 outputs light 22 at a wavelength of 280 nanometers. Beam 22 passes through a partially-silvered mirror 23. Partially-silvered mirror 23 has the characteristic of reflecting only a very small portion of beam 22. In accordance with the preferred embodiment of the invention, partially-silvered mirror 23 reflects only as much of beam 22 as is necessary to generate a clear signal for use as a reference beam 25, as will be described below. Depending upon the nature of the reference signal detector optics and detector electronics, partially-silvered mirror 23 may reflect as little as two or three percent of beam 22. It is desirable to minimize the percentage of beam 22 which is diverted away from sample 18 to form reference beam 25, in order that the maximum amount of energy from beam 22 falls on sample 18 and, accordingly, the maximum amount of fluorescence radiation is produced for detection by the system.

That portion of beam 22 which is not reflected by partially silvered mirror 23 passes through partially silvered mirror 23 to form sample illuminating beam 26 which is reflected by a half-silvered mirror 24 toward sample 18. Light passing to sample 18, and output emission light 48 from sample 18 are both filtered by lens 27.

Light emitting diode 20 is driven by a frequency synthesizer 30. Thus, frequency synthesizer 30 is caused to modulate the output of light emitting diode 20. Light emitting diode 20, which may emit ultraviolet radiation in the 300-400 mm range, stimulates the emission of fluorescence light 48, output by sample 18, which includes modulation and phase information. The same is mixed with a heterodyne or homodyne frequency signal to output demodulated frequency and phase information. The heterodyne or homodyne signal is provided by a heterodyne frequency synthesizer 34 which, together with synthesizer 30 may be driven by a common master oscillator 28.

It is noted that the arrangement including partially-silvered mirrors illustrates an example of the inventive instrument. It is also to be understood that the inventive apparatus and method may be applied to other types of fluorescence systems.

As noted above, the inventive system relies upon a fluorescence signal stimulated by a modulated excitation light source. The same is achieved through the use of a fundamental oscillator 28 operating at the desired modulation frequency, typically in the range of 5 MHz. The output of fundamental oscillator 28 is sent to a frequency synthesizer 30 which generates a plurality of other frequencies. In accordance with one embodiment of the invention, frequency synthesizer 30 will output a signal at 5 MHz and at multiples of 5 MHz ranging as high as 300 MHz or higher. In accordance of the present invention, however, it is contemplated that the frequencies of signals output by frequency synthesizer 30 may have other values, as may be convenient and/or efficient to generate, and/or process as described below, preferably provided that the desired range of modulation frequencies is covered with enough data points to perform a least squares curve fitting operation upon the data points within a desired statistical confidence interval.

In particular, in accordance with the invention, the method of least squares is used to fit a curve as close as possible to experimental data points produced by the system by minimizing the sum of the squares of the deviations of the experimental data points from the curve. In the case where the derivation of a curve describing the mathematical relationship between frequency and either modulation or phase, the functional type (linear, quadratic, exponential, sum of two exponentials, etc.,) is known, the method of least squares is used to determine the parameters of a general equation of that category.

Other statistical methods may also be used. In addition to estimating the parameters of the equation, the system may also be used to calculate standard error and a confidence interval. In addition, the inventive system 10 may be used even where there is no particular functional type that can be postulated as a starting point for the calculation. In such a case, standard fitting procedures may be used to gain insight into the subject matter under study. In addition, qualitative information respecting physical processes, for example as they vary over time, may be more easily understood after performance of a method of least squares approximation.

It is noted that a continuous wave source with either an intrinsic or external modulator, in accordance with this embodiment of the invention has a signal generator or synthesizer producing multiple harmonics.

Generally, a pulsed source only requires a fundamental frequency. The transform of a pulse is multiple coherent harmonics. In accordance with the invention, a pulsed source and a synthesizer controlling an array detector can be present in any system. Moreover, multiple synthesizers may be synchronized.

In accordance with the invention, the output of frequency synthesizer 30 is adjusted to be the sum of electrical energy at the fundamental and other frequency synthesizer frequencies. The energy at the fundamental frequency may be understood as a first optical drive signal component. The energy at the next highest frequency may be understood as a second optical drive signal component. The electrical energy at the third highest frequency may be understood as a third optical drive signal component, and so on through the range of frequencies output by frequency synthesizer 30.

The output of synthesizer 30 is sent to light emitting diode 20 which emits optical energy at the above or with any desired optical wavelength, but modulated in intensity by the output of synthesizer 30, which constitutes a sum of the various frequency signals generated by frequency synthesizer 30.

Heterodyne frequency synthesizer 34 is synchronized to the output of fundamental oscillator 28 and outputs a plurality of heterodyne signals. There is a heterodyne signal associated with each of the output signals generated by frequency synthesizer 30. The frequency of each of these heterodyne signals is slightly different from the frequency of its associated optical drive signal. The construction of heterodyne frequency synthesizer 34 is conventional and similar to that of frequency synthesizer 30. Each modulation and heterodyne signal pair may preferably have a unique low frequency product. Thus, the difference in modulating frequencies is different for each associated optical drive signal and its respective heterodyne signal, allowing the digital filters to individually separate modulation products for each of the optical drive signals at their respective frequencies. Thus, the first pair may comprise an output signal at 5 MHz and an associated heterodyne signal at 5.000005 MHz. The second pair may be 10 MHz and 10.000010 MHz, and so forth.

This difference may be, for example, 5 Hz for the first optical drive signal, 10 Hz for the second optical drive signal, 15 Hz for the third optical drive signal, and so forth.

It is noted that, in accordance in the invention, a single frequency synthesizer may perform the combined function of frequency synthesizer 30 and heterodyne frequency synthesizer 34.

The output of the heterodyne frequency synthesizer 34 is coupled to a sample image intensifier tube 38. The output of heterodyne frequency synthesizer 34 is also coupled to a reference intensifier tube 40.

As described above, a portion 26 of light beam 22 illuminates a sample 18 which may include, for example, a protein. That portion 26 of the light emitted from light emitting diode 20 is reflected by a half-silvered mirror 24 toward focusing optic 27 and sample 18, passing through transparent slide cover 16. When the protein in sample 18 is illuminated by light 26 from light emitting diode 20, the molecules comprising the protein are excited and fluoresce, emitting fluorescent radiation 48. Fluorescent radiation 48 is lower in energy than excitation source light 26, and, accordingly, it is of longer wavelength.

In addition to fluorescent radiation 48, a portion of light 26 may be reflected in various directions as light 50. Light 50, because it is simply reflected light, has the same wavelength as the excitation source light 22. A portion of both fluorescent radiation 48 and reflected excitation source light 50 travels along a path 52 toward microscope focusing optics 54, shown diagrammatically as a simple convex lens. In practice, microscope focusing optics 54 comprises a plurality of lenses in a confocal configuration, and includes a number of masks to achieve the desired confocal characteristic. In particular, the desired confocal characteristic achieves focusing of objects in a narrow range of focus which consists of a planar volume of relatively shallow depth in a manner well-known in the art. The object of the use of the inventive fluorescence microscope system 10 is to view a cross-section of the object, such as protein under view.

Microscope focusing optic 54 focuses an image of the specimen under observation including both fluorescent radiation 48 and reflected excitation light 50 (if it is not removed by post filtering) on the sensitive face 60 of image intensifier tube 38. During the normal operation of image intensifier tube 38, the optical image stimulates the formation of an electron image which is accelerated and triggers an avalanche to form an amplified image on the output face 61 of image intensifier tube 38. If desired, because of the relatively low level of fluorescent radiation 48 from a particular sample, reflected excitation light 50 may also optionally be blocked by a band-reject filter 62.

As discussed above, fluorescent radiation 48 has an amplitude and phase characteristic which varies from that of the excitation light 22 produced by light emitting diode 20. However, in order to measure this difference, a small sample of the excitation light 22 reflected by partially-silvered mirror 23 as sample light 25 must be measured. Accordingly, sample light 25 is brought by focusing optics 64 onto the sensitive face 66 of an intensifier tube 40. The sample light 25 brought to sensitive face 66 is accelerated and amplified to form an image on the output face 68 of image intensifier tube 40.

It is necessary for the amplified images on output face 61 to be compared to the light on output face 68 in order to determine modulation and phase information. This is done by providing output face 61 with a CCD detector 70, for example a 250 element by 250 element CCD or other suitable detector, preferably with a size and resolution matched to the output of image intensifier tube 38. The output of CCD 70 is thus an image of that portion of the protein focused by focusing optics 54 on sensitive face 60.

In similar fashion, output face 68 of image intensifier tube 40 is provided with a CCD detector 72, substantially identical to CCD 70. The output of CCD 72 is thus an image of that portion of the reference light traveling along path 25 and focused by focusing optics 64 on sensitive face 66 and serves as a reference with respect to which the sample image data may be compared to generate modulation and phase image information.

The outputs of image intensifier tubes 38 and 40 are sent to a computer interface board 74 on a computer 76. Using conventional filtering techniques, interface board 74 and computer 76 (controlled by filter software 78) together separate out the amplitude and phase information for both the reference beam 25 and fluorescent radiation 48, and generate amplitude (modulation) and phase information for the fluorescent light emitted by protein in sample 18. In addition, because this information is associated with two-dimensional spatial data in a given plane of focus, the fluorescence characteristic may be graphically shown on an output device 80 for visual or intuitive analysis and/or numerically processed with any desired criteria to achieve any desired quantitative or qualitative output.

Before using the inventive system to perform a measurement on a sample, it is necessary to calibrate the system. This is done by first using, in place of a sample, a standard consisting of a zero lifetime scattering solution. When the instrument measures the zero lifetime scattering solution, it creates a set of normalizing phase and modulation standard values which function as a standard. These normalized phase and modulation values, obtained using the zero lifetime scattering solution standard, are compared to measured phase and modulation values created by the system when it measures the sample. The system generates the phase and modulation standard values in the same way in which it measures phase and modulation values for a sample, as will be described in detail below. The actual phase and modulation value for a particular point on the sample is the difference, respectively, between the phase and modulation values generated for the point on the sample and the phase and modulation value generated for the same point using the zero lifetime scattering solution standard.

During operation of the inventive system to measure the characteristics of a sample, light emitting diode 20 is excited to produce modulated light. A small portion of the modulated light is reflected by partially-silvered mirror 23. This reflected light takes the form of light 25 which is sent through optics 64 to sensitive face 66 of intensifier tube 40. CCD 72 then forms a reference modulated electrical signal. In the instant example of a 250 by 250 element image intensifier tube 40 driving a 250 by 250 element CCD 72, this reference modulated electrical signal takes the form of 62,500 individual reference signals, one corresponding to each element in CCD 72. All of these 62,500 individual signals each serve as a reference signal and are downloaded in a conventional manner and sent to computer 26 via interface board 74.

As may be understood from the above, an intensified image falls on the front face 86 of CCD 70. CCD 70 then forms a measurement modulated electrical signal. In the instant example of a 250 by 250 element image intensifier tube 38 driving a 250 by 250 element CCD 70, this reference modulated electrical signal takes the form of 62,500 individual measurement signals, one corresponding to each element in CCD 70. Each of the 62,500 individual measurement signals is associated with one of the 62,500 individual reference signals output from CCD 72. These 62,500 individual signals each serve as a reference signal and are downloaded in a conventional manner and sent to computer 26 via an interface board 74.

In accordance with the preferred embodiment of the invention, each one of the 62,500 individual multifrequency measurement signals (for example, each containing a hundred single frequency signals, corresponding to a hundred excitation frequency modulation components associated with each pixel on the CCD array) is compared to its respective one of the 62,500 individual reference signals to generate phase and modulation information for the point on the image associated with the particular individual measurement signal and the point on the protein in sample 18 measured by the respective individual measurement signal. This is done by electrically filtering the output of each pixel to separate out the difference frequency modulation products (one hundred in the example of fifty modulation frequencies).

Thus, each pixel generates a plurality of phase measurements, one for each of the excitation frequencies. In addition, each pixel generates a plurality of modulation measurements for these frequencies. This may be better understood when it is recognized that image intensifiers 38 and 40 act as mixers, mixing each of the heterodyne signals and its respective measurement signal.

Figure 7:
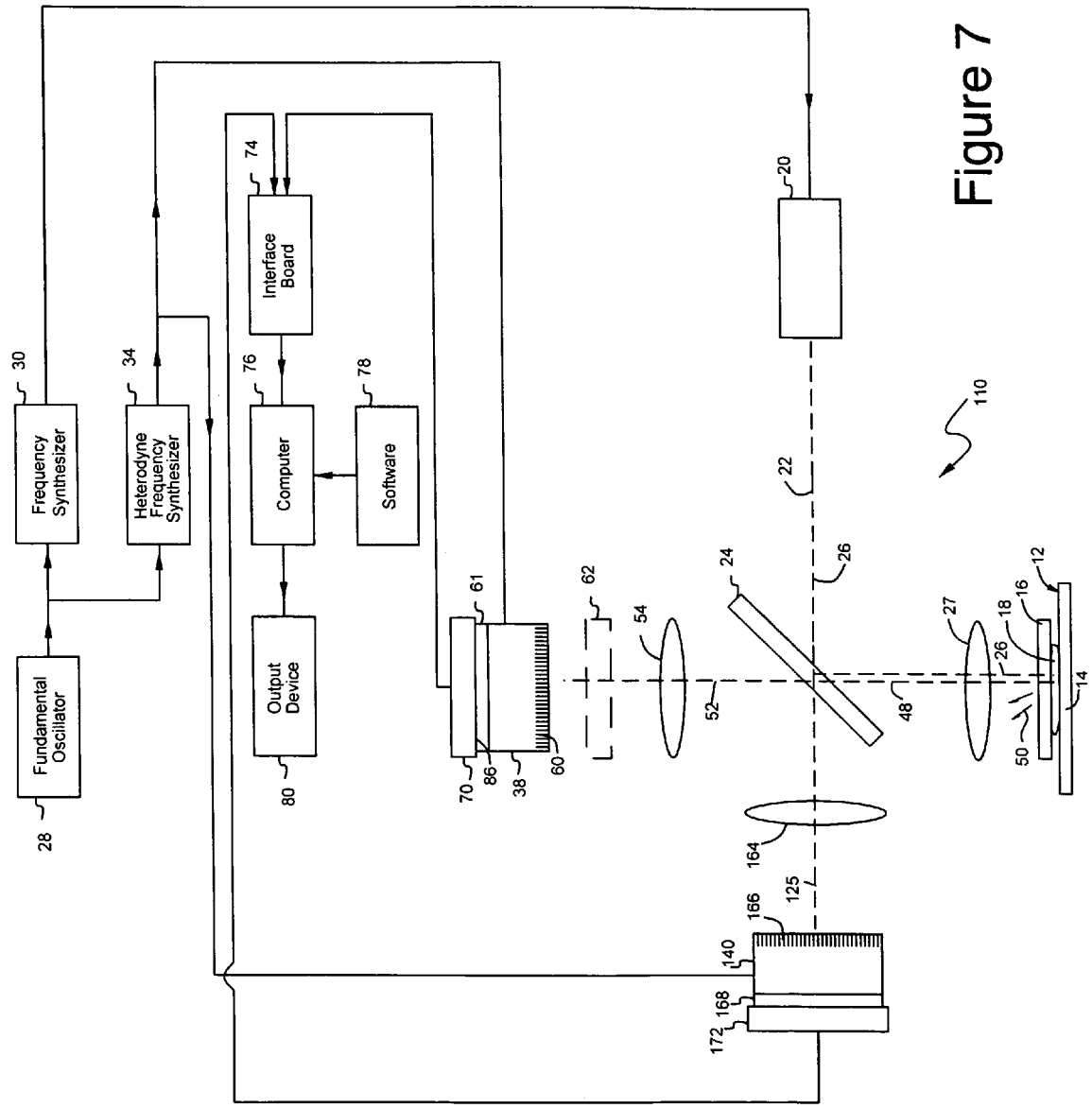
FIG. 7 is an alternative system in accordance with the invention.

FIG. 7 is an alternative embodiment of the system 110 of the invention where analogous parts are given numbers one hundred higher than those of the FIG. 6 embodiment. Here, a portion of the passed light created by beamsplitter 24 is used to provide reference light 125.

While an illustrative embodiment of the invention has been disclosed, it is understood that various modifications and applications of the inventive technique will be apparent to those of ordinary skill in the art based on the instant disclosure. For example, the inventive method may be used to study not only decay kinetics as discussed in detail above, but may also be applied to emission spectroscopy, microscopy, imaging and sensing using steady-state, modulated and pulsed modes of operation.

The invention claimed is:

1. A method of spectrographic measurement, comprising:
   (a) generating light energy using a solid state low capacitance excitation source, said light energy being caused to fall on a sample to be assayed, causing said sample to output an output optical signal;
   (b) generating a plurality of modulation frequencies;
   (c) generating a plurality of heterodyne frequencies to form a set of heterodyne signals at said heterodyne frequencies, each of said heterodyne frequencies being associated with one of said modulation frequencies;
   (d) coupling said modulation frequencies to said excitation source, causing said excitation source to generate excitation energy modulated in intensity in proportion to said modulation frequencies;
   (e) sampling a portion of said light energy generated using the solid state low capacitance excitation source to form a reference excitation signal;
   (f) focusing said output optical signal as an image modulated with said plurality of modulation frequencies on an image intensifier;
   (g) intensifying said image to form an intensified image modulated with said plurality of modulation frequencies;
   (h) receiving said intensified image modulated with said plurality of modulation frequencies on a multielement optical detector;
   (i) generating a plurality of measurement signals using said multielement optical detector, each measurement signal associated with one of said elements;
   (j) for each measurement signal associated with one of said elements of said multielement optical detector, said measurement signal being mixed with its respective one of said heterodyne signals to generate a plurality of low-frequency measurement modulation products, a low-frequency measurement modulation product being associated with each of said modulation frequencies and comprising the difference between a modulation frequency and its associated heterodyne frequency and having a measurement amplitude and phase;
   (k) mixing said reference excitation signal with said respective heterodyne signal to generate a plurality of reference modulation products, a reference modulation product being associated with each of said modulation frequencies and comprising the difference between a modulation frequency and its associated heterodyne frequency and having a reference amplitude and phase, each of said reference modulation products being associated with one of said measurement modulation products; and (l) for each of said plurality of low-frequency measurement modulation products, comparing said low-frequency measurement modulation product to its associated reference modulation product to generate an output signal indicating characteristics of said sample at the region on said sample associated with each of said elements.

2. The method of claim 1, wherein said output signal is numerically processed to generate changes over time.

3. The method of claim 1, wherein said output signal may be graphically displayed.

4. The method of claim 1, wherein said output signal is numerically processed to generate a desired parameter.

5. The method of claim 1, wherein said excitation source is substantially incoherent.

6. The method of claim 1, wherein said output optical signal comprises fluorescent energy from said sample.

7. The method as in claim 1, wherein said modulation frequencies are harmonically related.

8. The method as in claim 1, wherein said excitation source is a substantially incoherent source whose output is modulated by a Pockel's cell.

9. The method as in claim 1, wherein said excitation source is a substantially incoherent source whose output is a pulsed.

10. The method as in claim 9, wherein said excitation source is a pulsed-dye source.

11. The method as in claim 1, wherein said excitation source is a light emitting diode.

12. The method as in claim 1, wherein said reference modulation products are low-frequency reference modulation products output during said mixing of said reference excitation signal with said respective heterodyne signal.

13. The method as in claim 12, wherein said comparison is done by measuring the relative phase and amplitude of said low-frequency measurement modulation product as compared to said low-frequency reference modulation product and generating a modulation data point and a phase data point.

14. The method as in claim 13, further comprising:
(m) for each element, fitting said modulation data points to a first curve using the method of least squares;
(n) for each element fitting said phase data points to a second curve using the method of least squares;
(o) comparing said first and second curves to a database to determine characteristics of said sample; and
(p) displaying said characteristics.

15. The method of claim 1, wherein before said excitation energy output by said excitation source is caused to fall on said sample to be measured, the system is calibrated by first using, in place of said sample, a standard consisting of a zero lifetime scattering solution to create a set of normalizing phase and modulation standard values against which said phase and modulation values for said sample are measured.

16. A method of spectrographic measurement, comprising:
(a) generating substantially incoherent excitation energy in the form of light energy using a solid state excitation source, said light energy being caused to fall on a sample to be assayed, causing said sample to output an output optical signal;
(b) generating a plurality of modulation frequencies;
(c) generating a plurality of heterodyne frequencies to form a set of heterodyne signals at said heterodyne frequencies, each of said heterodyne frequencies being associated with one of said modulation frequencies;

(d) coupling said modulation frequencies to said excitation source, causing said excitation source to generate excitation energy modulated in intensity in proportion to said modulation frequencies;
(e) sampling a portion of said substantially incoherent excitation energy to form a substantially incoherent reference excitation signal;
(f) focusing said output optical signal as an image modulated with said plurality of modulation frequencies on an image intensifier;
(g) intensifying said image to form an intensified image modulated with said plurality of modulation frequencies;
(h) receiving said intensified image modulated with said plurality of modulation frequencies on a multielement optical detector;
(i) generating a plurality of measurement signals using said multielement optical detector, each measurement signal associated with a single one of said elements; and
(j) for each measurement signal associated with a single one of said elements of said multielement optical detector, comparing the output of said elements to a standard to generate an output signal indicating characteristics of said sample at the region on said sample associated with each of said elements.

17. Apparatus for performing fluorescence measurement, comprising:
(a) a solid state light source generating substantially incoherent excitation energy in a range below 300 nm, oriented to illuminate a sample to be measured and cause said sample to emit fluorescent energy;
(b) a frequency generator generating a plurality of modulation frequencies and a plurality of heterodyne frequencies, each of said heterodyne frequencies being associated with one of said modulation frequencies said frequency generator being coupled to said excitation source, whereby said source generates excitation energy modulated in intensity in proportion to said modulation frequencies;
(c) an optical member positioned to receive said substantially incoherent excitation energy and divert a portion of said substantially incoherent excitation energy, said portion of said substantially incoherent excitation energy forming a substantially incoherent reference excitation signal;
(d) focusing optics positioned to receive said fluorescent energy and form an image modulated with said plurality of modulation frequencies;
(e) an image intensifier positioned to receive said image, said image intensifier having an output for outputting an intensified image modulated with said plurality of modulation frequencies;
(f) a multielement optical detector positioned to receive said intensified image modulated with said plurality of modulation frequencies and generating response thereto a plurality of measurement signals, each associated with a single one of said elements;
(g) a mixer coupled to receive each of said heterodyne frequencies and producing in response to said image and said heterodyne frequencies a plurality of low-frequency measurement modulation products, a low-frequency measurement modulation product being associated with each of said modulation frequencies and comprising the difference between a modulation frequency and its associated heterodyne frequency and having a measurement amplitude; and (h) a mixer coupled to said substantially incoherent reference excitation signals and said heterodyne frequencies to generate a plurality of low-frequency reference modulation products, a low-frequency reference modulation product being associated with each of said modulation frequencies and comprising the difference between a modulation frequency and its associated heterodyne frequency and having a reference amplitude and phase, each of said low frequency reference modulation products being associated with one of said measurement modulation products, each of said low-frequency measurement modulation products, and their associated low-frequency reference modulation products indicating phase and the modulation information.

18. Apparatus as in claim 17, wherein optical said member is a partially silvered mirror.

19. Apparatus as in claim 17, wherein optical said member is a prism.

20. Apparatus as in claim 17, wherein said image intensifiers function as mixers.

21. Apparatus for performing fluorescence measurements, comprising:
(a) a solid state low capacitance light source generating substantially incoherent excitation energy in the range below 300 nm, oriented to illuminate a sample to be measured and cause said sample to emit fluorescent energy;
(b) a frequency generator generating a plurality of modulation frequencies and a plurality of heterodyne frequencies; each of said heterodyne frequencies being associated with one of said modulation frequencies said frequency generator being coupled to said excitation source, whereby said source generates excitation energy modulated in intensity in proportion to said modulation frequencies;
(c) an optical member positioned to receive said substantially incoherent excitation energy and divert a portion of said substantially incoherent excitation energy, said portion of said substantially incoherent excitation energy forming a substantially incoherent reference excitation signal;
(d) focusing optics positioned to receive said fluorescent energy and form an image modulated with said plurality of modulation frequencies;
(e) an image intensifier positioned to receive said image, said image intensifier having an output for outputting an intensified image modulated with said plurality of modulation frequencies;
(f) a multielement optical detector positioned to receive said intensified image modulated with said plurality of modulation frequencies and generating a response thereto a plurality of measurement signals, each associated with a one of said elements; and
(g) a calculating device coupled to said measurement signals, said heterodyne signals and said substantially incoherent reference excitation signals and configured to extract phase and modulation information.

22. A method of fluorescence measurement comprising:
(a) generating light energy in the form of substantially incoherent excitation energy in a range below 300 nm output by an excitation source, said substantially incoherent excitation energy being caused to fall on a sample to be measured and cause said sample to emit fluorescent energy;
(b) generating a plurality of modulation frequencies;
(c) generating a plurality of heterodyne frequencies to form a set of heterodyne signals at said heterodyne frequencies, each of said heterodyne frequencies being associated with one of said modulation frequencies;
(d) coupling said modulation frequencies to said excitation source causing said source to generate excitation energy modulated in intensity in proportion to said modulation frequencies;
(e) sampling a portion of said substantially incoherent excitation energy to form a substantially incoherent reference excitation signal;
(f) focusing said fluorescent energy as an image modulated with said plurality of modulation frequencies on an image intensifier;
(g) intensifying said image to form an intensified image modulated with said plurality of modulation frequencies;
(h) receiving said intensified image modulated with said plurality of modulation frequencies on a multielement optical detector;
(i) generating a plurality of measurement signals using said multielement optical detector, a signal being output from each of the elements of said multielement, optical detector, each measurement signal associated with one of said elements;
(j) for each measurement signal associated with one of said elements of said multielement optical detector, said measurement signal being mixed with its respective one of said heterodyne frequencies to generate a plurality of low-frequency measurement modulation products, a low-frequency measurement modulation product being associated with each of said modulation frequencies and comprising the difference between a modulation frequency and its associated heterodyne frequency and having a measurement amplitude and phase;
(k) mixing said substantially incoherent reference excitation signal with its respective one of said heterodyne frequencies to generate a plurality of low-frequency reference modulation products, a low-frequency reference modulation product being associated with each of said modulation frequencies and comprising the difference between a modulation frequency and its associated heterodyne frequency and having a reference amplitude and phase, each of said low-frequency reference modulation products being associated with one of said measurement modulation products;
(l) for each of said plurality of low-frequency measurement modulation products, comparing said low-frequency measurement modulation product to its associated low-frequency reference modulation product to measure the relative phase and amplitude of said low-frequency measurement modulation product as compared to said low-frequency reference modulation product and generating a modulation data point and a phase data point;
(m) for each element, fitting said modulation data points to a first curve;
(n) for each element fitting said phase data points to a second curve;
(o) comparing said first and second curves to a database to determine characteristics of said sample; and
(p) displaying said characteristics; and generating a reference standard modulation data point and a reference standard phase data point using a zero lifetime standard by:
(q) causing said generated light energy in the form of substantially incoherent excitation energy output by said excitation source, to fall on a zero lifetime standard causing said sample to output a reference standard optical signal;

(r) generating a plurality of modulation frequencies;
(s) generating a plurality of heterodyne frequencies to form a set of heterodyne signals at said heterodyne frequencies, each of said heterodyne frequencies being associated with one of said modulation frequencies;
(t) coupling said modulation frequencies to said excitation source causing said source to generate excitation energy modulated in intensity in proportion to said modulation frequencies;
(u) sampling a portion of said substantially incoherent excitation energy to form a reference substantially incoherent excitation signal;
(v) focusing said reference standard optical signal as a standard image modulated with said plurality of modulation frequencies on said image intensifier;
(w) intensifying said standard image to form an intensified standard image modulated with said plurality of modulation frequencies;
(x) receiving said intensified standard image modulated with said plurality of modulation frequencies on said multielement optical detector;
(y) generating a plurality of measurement signals using said multielement optical detector, a single signal being output from each of the elements of said multielement optical detector, each measurement signal associated with a single one of said elements;
(z) for each measurement signal associated with one of said elements of said multielement optical detector, said measurement signal being mixed with said heterodyne signal to generate a plurality of low-frequency measurement modulation products, one low-frequency measurement modulation product being associated with each of said modulation frequencies and comprising the difference between a single modulation frequency and its associated heterodyne frequency and having a measurement amplitude and phase;
(aa) mixing said substantially incoherent reference excitation signal with said heterodyne signal to generate a plurality of low-frequency reference modulation products, a low-frequency reference modulation product being associated with each of said modulation frequencies and comprising the difference between a modulation frequency and its associated heterodyne signal and having a reference amplitude and phase, each of said low-frequency reference modulation products being associated with one of said measurement modulation products; and
(bb) for each of said plurality of low-frequency measurement modulation products, comparing said low-frequency measurement modulation product to its associated low-frequency reference modulation product to measure the relative phase and amplitude of said low-frequency measurement modulation product as compared to said low-frequency reference modulation product and generating a reference standard modulation data point used to generate phase and modulation data points and a reference standard phase data point.

* * * * *

UNITED STATES PATENT AND TRADEMARK OFFICE
CERTIFICATE OF CORRECTION

PATENT NO. : 7,582,882 B2  Page 1 of 1
APPLICATION NO. : 11/184407
DATED : September 1, 2009
INVENTOR(S) : David McLoskey et al.

It is certified that error appears in the above-identified patent and that said Letters Patent is hereby corrected as shown below:

Column 14, Line 19, Claim 16:

After "associated with"

Delete "a single"

Column 14, Line 20, Claim 16:

After "associated with"

Delete "a single"

Column 14, Line 67, Claim 17:

After "measurement amplitude"

Insert -- and phase --.

Signed and Sealed this

First Day of December, 2009

David J. Kappos
*Director of the United States Patent and Trademark Office*